US012596754B1

(12) United States Patent
Wang et al.

(10) Patent No.: US 12,596,754 B1
(45) Date of Patent: Apr. 7, 2026

(54) ARTIFICIAL INTELLIGENCE POWERED SEARCH PLATFORM FOR END-TO-END SERVICES IN DIGITAL HEALTHCARE

(71) Applicant: Humana Inc., Louisville, KY (US)

(72) Inventors: Guan Wang, Louisville, KY (US); Likitha Punati, Louisville, KY (US); Aarthi Shanmugasundaram, Louisville, KY (US); Shiva Nagaraju Kuricheti, Louisville, KY (US)

(73) Assignee: Humana Inc., Louisville, KY (US)

( * ) Notice: Subject to any disclaimer, the term of this patent is extended or adjusted under 35 U.S.C. 154(b) by 0 days.

(21) Appl. No.: 18/883,290

(22) Filed: Sep. 12, 2024

(51) Int. Cl.
G06F 16/951 (2019.01)
G06F 16/9538 (2019.01)
G16H 50/70 (2018.01)

(52) U.S. Cl.
CPC ........ G06F 16/951 (2019.01); G06F 16/9538 (2019.01); G16H 50/70 (2018.01)

(58) Field of Classification Search
CPC ............................. G06F 16/951; G06F 16/9538
See application file for complete search history.

(56) References Cited

U.S. PATENT DOCUMENTS

| | | | |
|---|---|---|---|
| 2024/0281410 A1* | 8/2024 | Williams | G06F 16/122 |
| 2024/0362208 A1* | 10/2024 | Naufel | G06F 16/243 |
| 2024/0370339 A1* | 11/2024 | Statton | G06F 11/1458 |
| 2024/0379226 A1* | 11/2024 | Annangi | G06N 3/084 |
| 2025/0021908 A1* | 1/2025 | Ben Messaoud | G06Q 50/205 |
| 2025/0190507 A1* | 6/2025 | Gadit | G06F 16/951 |

* cited by examiner

*Primary Examiner* — Courtney Harmon
(74) *Attorney, Agent, or Firm* — Standley Law Group LLP; Jeffrey S. Standley; Adam J. Smith

(57) ABSTRACT

Systems and methods for providing an artificial intelligence powered search platform ("platform") for providing end-to-end services in digital healthcare, include gathering, at the platform, data from a plurality of data sources by way of a plurality of data collection pipelines, processing, at the platform, the data gathered from the plurality of data sources by way of the plurality of data collection pipelines, including transformation, enrichment, and ingestion of the data into one or more common formats, receiving queries from user at the platform, processing the queries, at the platform, using an intent based engine, searching, by way of the platform, the data based on the queries, and providing the results to the users, by way of the platform, the results including generative summaries and direct links to certain of the plurality of data sources used to create the generative summaries.

16 Claims, 15 Drawing Sheets

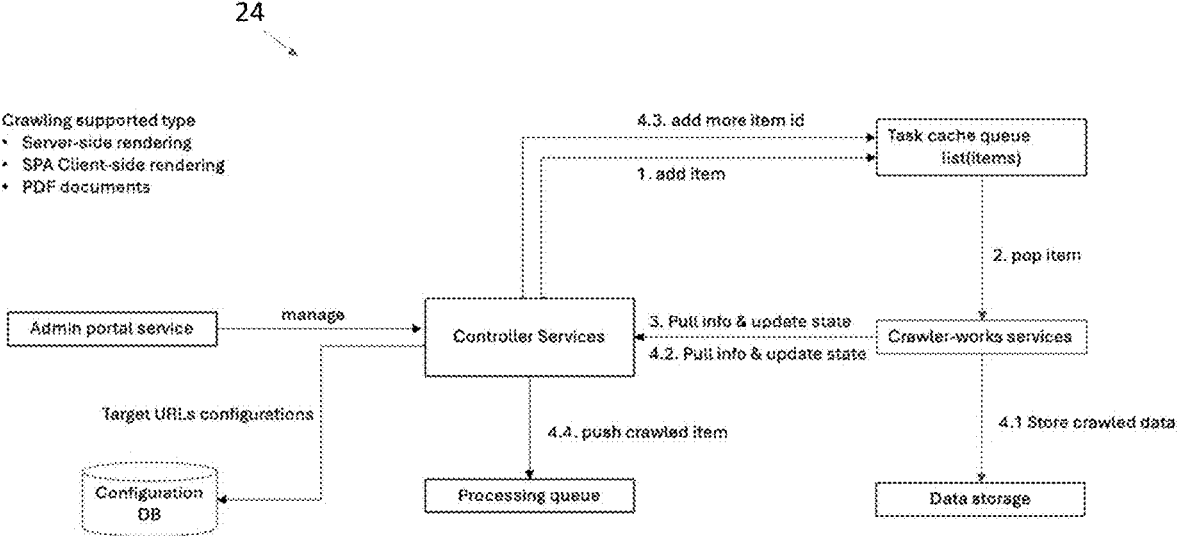

24

Crawling supported type
* Server-side rendering
* SPA Client-side rendering
* PDF documents 4.3. add more item id Task cache queue
list(items)

1. add item

Admin portal service — manage → Controller Services

3. Pull info & update state 4.2. Pull info & update state 2. pop item

Crawler-works services

Target URLs configurations

Configuration DB 4.4. push crawled item

Processing queue 4.1 Store crawled data

Data storage

```
{
"timestamp": "timestamp",
"session_id": "String",
"index_name " : "String",
"query": "String",
"intent": "String",
"filtering": "String",
"is_draw": Boolean,
"is_search": Boolean
}
```

FIGURE 15

ARTIFICIAL INTELLIGENCE POWERED SEARCH PLATFORM FOR END-TO-END SERVICES IN DIGITAL HEALTHCARE

CROSS-REFERENCE TO RELATED APPLICATIONS

This application is filed as original and makes no priority claim.

TECHNICAL FIELD

Exemplary embodiments relate generally to systems and methods for providing an artificial intelligence ("AI") powered search platform for providing end-to-end services in digital healthcare.

BACKGROUND AND SUMMARY OF THE INVENTION

The healthcare industry relies heavily on accessing a broad range of information, including health care plans, formulary, claims, and patient records, by way of non-limiting example. Conventional methods of information retrieval are slow and ineffective, often causing delays and bottlenecks in decision-making and influencing patient outcomes. AI-driven smart search technology helps address these challenges. For instance, an integrated health portal requires advanced search functionalities to locate resources like member benefits and providers. Search results may provide direct links to pertinent documents for simplified navigation. Enhanced search capabilities are important for meeting the demand for precise results and link users with necessary resources. However, an effective search platform involves more than a search engine, AI-powered, or otherwise. It involves effective data collection, processing, ingestion, and the like. It encompasses multiple eco-systems, configurations, and orchestration processes. Proper development and deployment is complex, time-consuming, and tedious. Users prefer a search platform as a service so they do not have to worry about how data collection, processing, and ingestion work underneath, and can focus on their searching and data retrieval. Therefore, an AI-powered search platform as a service is advantageous for providing end-to-end services.

In addition to utilizing natural language processing and machine learning, an effective search platform should effectively gather and process data, intelligently handle files, enhance data quality, and regulate data access, among other considerations. The automation and synchronization of these tasks and processes are important to an effective search platform. An advanced search platform with such features is herein disclosed. The disclosed search platform and related systems and methods provides a user-friendly experience with features like web crawling, data pipelines, semantic search, and AI, among other features. The disclosed search platform and related systems and methods allow users to collect, arrange, and combine data from different sources using the self-service portal. The search interfaces may be personalized through the portal and easily added to user's devices, such as in the form of an installed application ("app").

Further features and advantages of the systems and methods disclosed herein, as well as the structure and operation of various aspects of the present disclosure, are described in detail below with reference to the accompanying figures.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical, similar, or equivalent features, and wherein:

FIG. 2 is a schematic diagram for a web-crawling module of the AI powered search platform of FIG. 1;

FIG. 15 is a schema for capturing query history for post search analytics for the AI powered search platform of FIG. 1.

DETAILED DESCRIPTION OF EXEMPLARY EMBODIMENT(S)

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

Embodiments of the invention are described herein with reference to illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Figure 1:
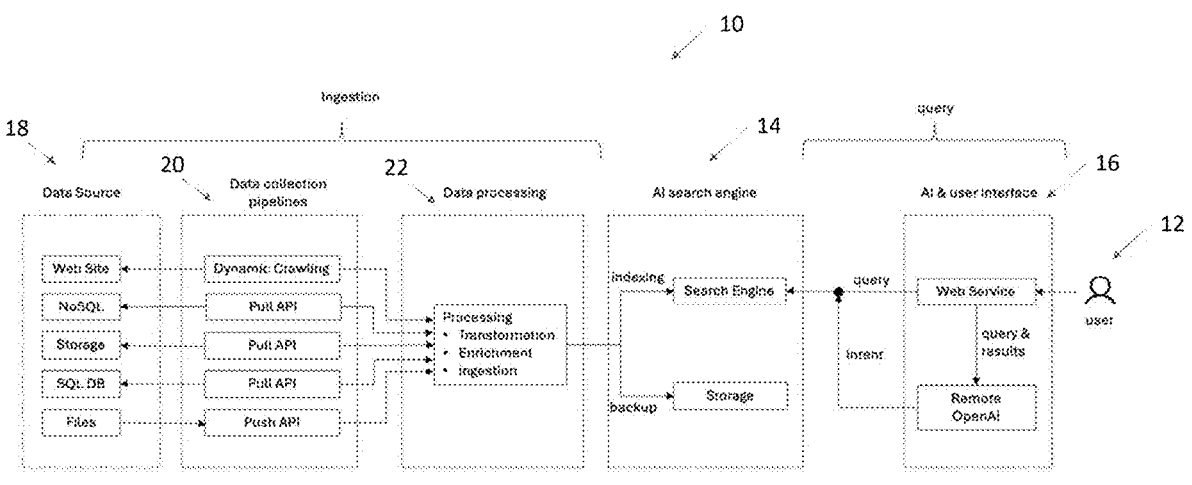
FIG. 1 is a schematic diagram of the AI powered search platform.

FIG. 1 illustrates an AI search and self-service platform 10 (hereinafter also the "platform") for end-to-end solutions, preferably in healthcare. This platform 10 enables users 12 to collect data from various sources and formats. The data collection process may involve web crawling, querying API services, uploading files, combinations thereof, or the like. Data processing may include transformation, enrichment, ingestion, and usage analytics. The AI search engine 14 may support semantic search, and queries may be conducted through web or API services. One or more AI features, including but not necessarily limited to, intent detection and/or generative summaries, may be integrated into the platform 10, such as in a secure environment with network security, data segregation, and data privacy controls at both index and document levels, by way of non-limiting example. The AI features may include, for example without limitation, those provided by OpenAI, Inc. of San Francisco, CA or other third parties. Scalability, observability, disaster recovery, data backup, combinations thereof, and the like are addressed for the production as further shown and/or described herein.

In exemplary embodiments, without limitation, the web-crawling may be capable of crawling static and dynamic web pages across domains, as well as embedded content (e.g., PDF files and images). HTML tags, path patterns, and XPath may be automatically excluded from the content. Runs may be scheduled, set rate limits may be established, and crawling stage and state via cache, queue, and database may be managed. The gathered data may be stored in a data lake for processing and ingestion.

In exemplary embodiments, without limitation, users 12 may access one or more user interfaces 16 of the platform 10, such as but not limited to web-based services. One or more AI features, such as intent detection, such as provided by OpenAI or other third parties, may be utilized with regard to submitted queries. These may include semantic analysis, intelligent autocomplete, filter application, image recognition, combinations thereof, and the like. The search engine 14 may be run against the query.

On the data ingestion side, data for the search engine 14 may be drawn from a plurality of sources 18, such as but not necessarily limited to, web site(s) and/or databases (e.g., NoSQL, SQL, servers, files, combinations thereof, or the like), among other sources. The data may be gathered through one or more data collection pipelines 20, which may be specific to the data source 18, though such is not necessarily required. Web crawling may be used for websites, and pull APIs may be utilized for various databases, by way of example. The data may be processed though one or more processing modules 22, which may include transformation, enrichment, and/or ingestion, by way of non-limiting example. The search engine 14 may include an indexed engine and a backup storage copy. In exemplary embodiments, without limitation, the two copies are provided at different cloud regions for high availability and disaster recovery. The collected data may include, for example without limitation, provider information, formulary information, coverage rules, demographic information, member identifying information, claim information, care codes, combinations thereof, or the like. While healthcare specific data is sometimes shown and/or described, other type or kinds of data may be utilized.

The search engine 14 supports semantic search, and may back up data during ingestion for index recreation. Queries may be made using web or API services. Intent detection may be integrated.

In exemplary embodiments, without limitation, the platform 10, is hosted remotely at one or more servers and is accessible by way of one or more applications provided at remote electronic devices associated with the users 12, such as smartphones, personal computers, laptops, tablets, combinations thereof, or the like. The platform 10 may be in connection with the various data sources 18, which may be provided at common or distinct databases, servers, electronic storage devices, or the like. Connections between the various components of the system 10 may be provided by way of the internet, intranets, cellular networks, combinations thereof, or the like.

In exemplary embodiments, without limitation, the AI-search engine 14 and some or all of the system 10 is provided on the user 12 facing side, and/or comprises a user-friendly, self-service portal for multiple tenants. All web crawling, data pipelines, semantic embedding, and search interface generation may be controlled in the portal. Users 12 may be able to collect, arrange, and combine data from different sources 18 using the self-service portal. The users 12 may be able to customize the search interfaces and easily add them to their apps.

Data Collection

Data collections from the various sources 18 may be accomplished through various pipelines 20 and/or techniques, which may include web site crawling, API service calling, file uploading, combinations thereof, or the like, by way of non-limiting example. The conversion and transformation of data formats may be automatically handled, such as by the pipelines 20.

File uploading may include format recognition (e.g., of JSON, JSONL, CSV, PDF, PNG, and/or JPEG). Optical character recognition (OCR) may be utilized to extract data fields from documents, such as images from PDFs, as well extract PDF tables in Markdown format and handle tables that span multiple pages, by way of non-limiting example.

Preferably, all data is converted by the platform 10 into one or more common formats, such as but not limited to JSON.

As illustrated with particular regard to FIG. 2, the data pipelines 20 may include a crawling module 24. The crawling module 24 may be established, managed, and/or executed in an at least partially automated fashion. Configurations may be stored in the database for reuse, crawling tasks may cached, such as to improve performance, crawling progress may be monitored in the process queue, and resulting data may be stored in the data storage for later retrieval.

Figure 3:
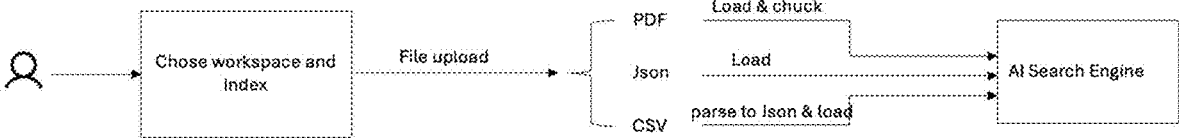
FIG. 3 is a schematic diagram for a file upload and ingestion module for the AI powered search platform of FIG. 1.

As illustrated with particular regard to FIG. 3, the data pipelines 20 may include an ingestion module 26. The ingestion module 26 may provide for uploading and ingesting files. Workspace and index collection settings may be automatically configured based on the user's 12 profile information, such as stored at a control database. Certain types files (e.g., PDF) may be chunked and converted, while other types of files (e.g., CSV) may be transformed into other file types (e.g., JSON) before being ingested into the search engine 14.

Search Operations

Figure 4:
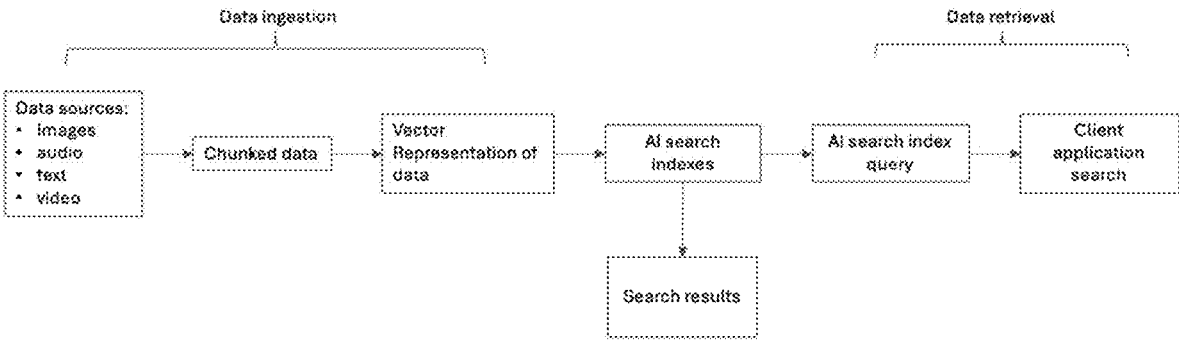
FIG. 4 is a schematic diagram for a semantic ingestion and query module for the AI powered search platform of FIG. 1.

As illustrated with particular regard to FIG. 4, search operations may involve data chunking, ingestion, intent detection, and query handling for semantic searching. Semantic ingestion and query may utilize machine learning to transform text, audio, or images into numerical representations, such as using vector representations of data. For example, without limitation, semantic ingestion and query may involve transforming text, audio, and/or images into numerical representations using machine learning to enhance search results. The diagram of FIG. 4 depicts, in an exemplary fashion, the flow of semantic vector search ingestion and query.

Figure 5:
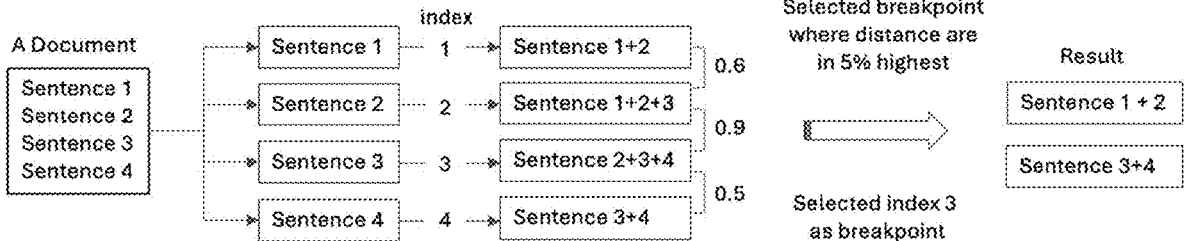
FIG. 5 is a flow chart for chunking large documents for the AI powered search platform of FIG. 1.

As illustrated with particular regard to FIG. 5, chunking large documents into smaller parts ensures efficient processing by embedding models. Original documents may be split per searchable domains, for example, and domain-relevant indexes may be created to assist with enhancing retrieval results in semantic search, such as by ensuring that text input remains within limits and segmenting content to provide efficient processing by embedding models for both ingestion and query conversions.

FIG. 5 provides non-limiting examples of chunking large documents into smaller ones while keeping the content relatively independent. In a semantic search, it may be important to split original documents per searchable domains. The created indexes may contain domain-relevant vectors that enhance the retrieval results quality. In the illustrated example, the vector distance between the sentences (1+2) and (1+2+3) is 0.6, between (1+2=3) and (2+3+4) is 0.9, and between (2+3+4) and (3:4) is 0.5. The longer the distance between the vectors, the more different in meaning. Thus, in the illustrated, non-limiting example, index 3 is selected as the breakpoint. The illustrated example is not intended to be limiting.

Figure 6:
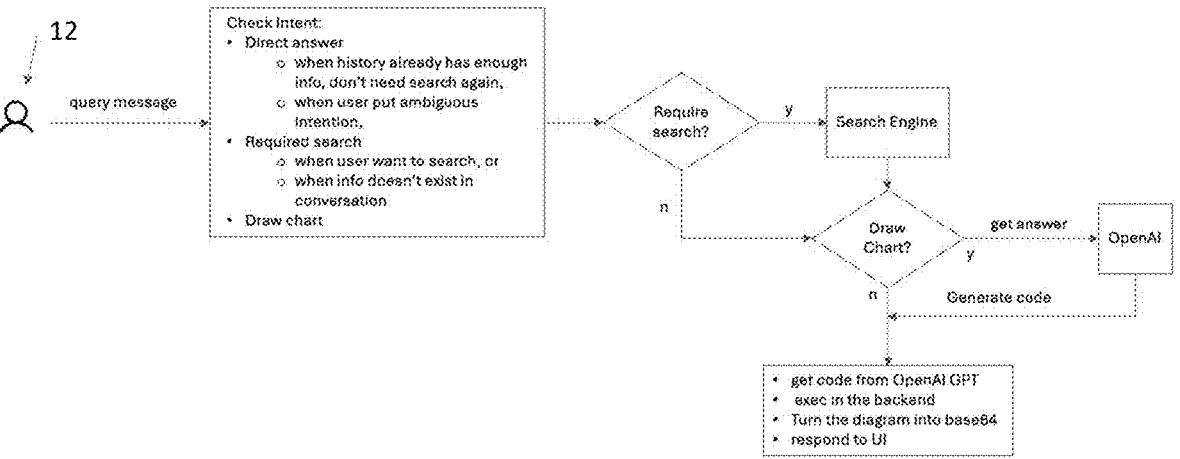
FIG. 6 is a flow chart for operating the semantic ingestion and query module for the AI powered search platform of FIG. 1.

The search engine 14 aims to provide the most relevant information possible in response to a user 12 query, such as in a generative response. However, the initial results may not always contain all the information the user 12 is seeking. To assist users 12 in gaining deeper insights, reference documents or links to additional information resources, such as from where some, all, or at least a majority, of the generative content was derived (e.g., the source file or files), may be generated by the system 10 for the user 12 to access as desired, such as illustrated with particular regard to FIG. 6. The platform 10 may be configured to convert the source data back to an original format or other user viewing friendly format for viewing (e.g., direct link to active website, HTML format, PDF format, etc.)

The semantic search processes may involve detecting intent, tracking history, and displaying search queries. Machine learning processing ("MLP") and/or natural language processing ("NLP") may be utilized to classify intent by associating words or sentences with specific purposes. The prompt may incorporate historical queries (e.g., searches, chat bot messages, etc.) as input and adds a sub-chain that reformulates the latest user question within the context of the query (e.g., multiple searches, chat) history. The history may be analyzed for context, patterns, combinations thereof, or the like using one or more AI techniques (e.g., pattern recognition, neural network, depth first search, breadth first search, A* searching, genetic algorithms, combinations thereof, or the like). Analyzing query history and tracking chat events may involve a series of steps, such as: identifying and uploading query history and chat events, passing them through event streaming processing as data points occur, allowing real-time reactions from downstream processes and automatic handling of start and stop processing is included. Search engine 14 indexing may be updated based on the analysis.

A presentation plugin may be employed to generate graphs that reveal patterns, trends, and relationships within complex data, in exemplary embodiments, without limitation.

End-to-End Self-Service

Figure 7:
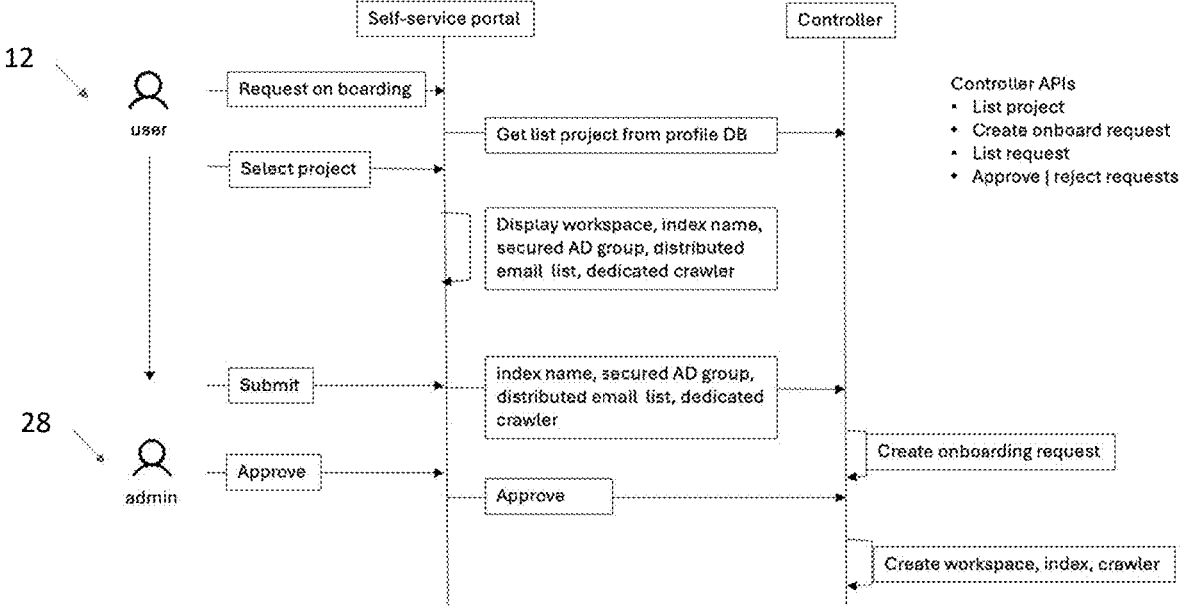
FIG. 7 is a flow chart for user onboarding for the AI powered search platform of FIG. 1.

As illustrated with particular regard to FIG. 7, a process flow may be employed by the system 10 for user 12 onboarding, workspace creation and index configurations, search API configuration and testing, and bot interface configuration and testing, in exemplary embodiments without limitation.

The process may be orchestrated and rendered with a self-service portal to provide a smooth, scalable, and successful onboarding process. User 12 attributes and access rights may be registered in a user database of the system 10 during the intake process, and may include secure AD group and/or distributed email list(s) by way of non-limiting example. Users 12 may request workspace(s), index collection name(s), and/or dedicated crawler(s), by way of example. After submitting the request, such as by filling out a form, submitted information may be automatically routed to an administrator user 28, such as by generating a notification for approval. Once approved, the requested workspace and crawler may be automatically created.

The workspaces may include various graphical user interfaces (GUIs) and/or human machine interface (HMI) objects, such as but not limited to, search bars, chat bots, virtual assistants, combinations thereof, or the like. Features may include intent detection, visuals and/or retry options for unsuccessful responses, combinations thereof, or the like. The appearance and user experience may be controlled by centralized content management libraries and may be set based on user 12 preferences.

In exemplary embodiments, without limitation, the search button and AI bot chat window interfaces are automatically generated for testing. They may be linked to user 12 profiles and permissions, and testing and verification tasks may be automatically scheduled with tracking and reporting for each test on the platform 10.

Figure 8:
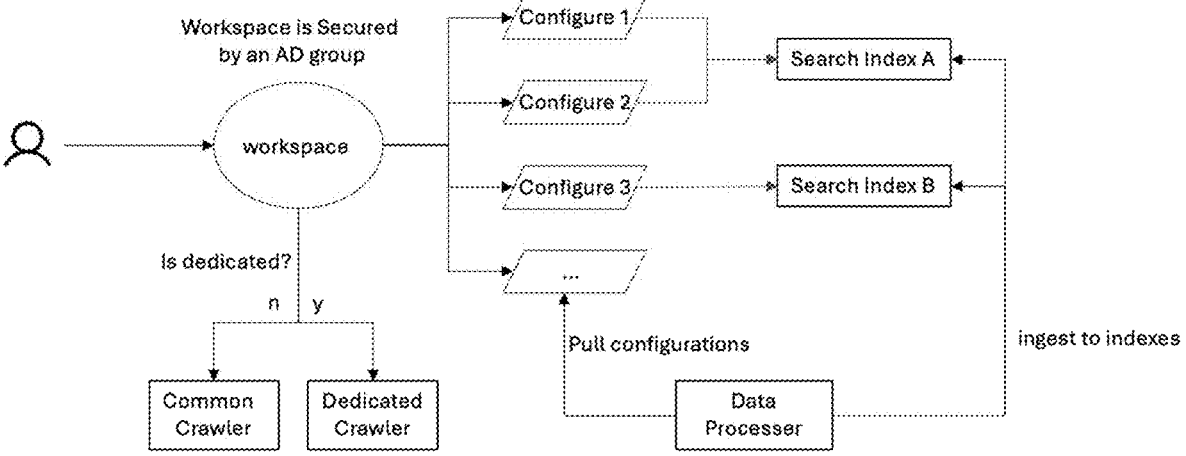
FIG. 8 is a flow chart for user configuration for the AI powered search platform of FIG. 1.

As illustrated with particular regard to FIG. 8, users 12 may set up the client search API interfaces, including node.js objects of the search button and AI bot conversion window, by way of example. Exemplary steps for selecting crawler type, setting up data processor, and client search API interfaces, such as node.js objects for search button and AI bot conversion window are s illustrated in FIG. 8 by way of non-limiting example.

Figure 9:
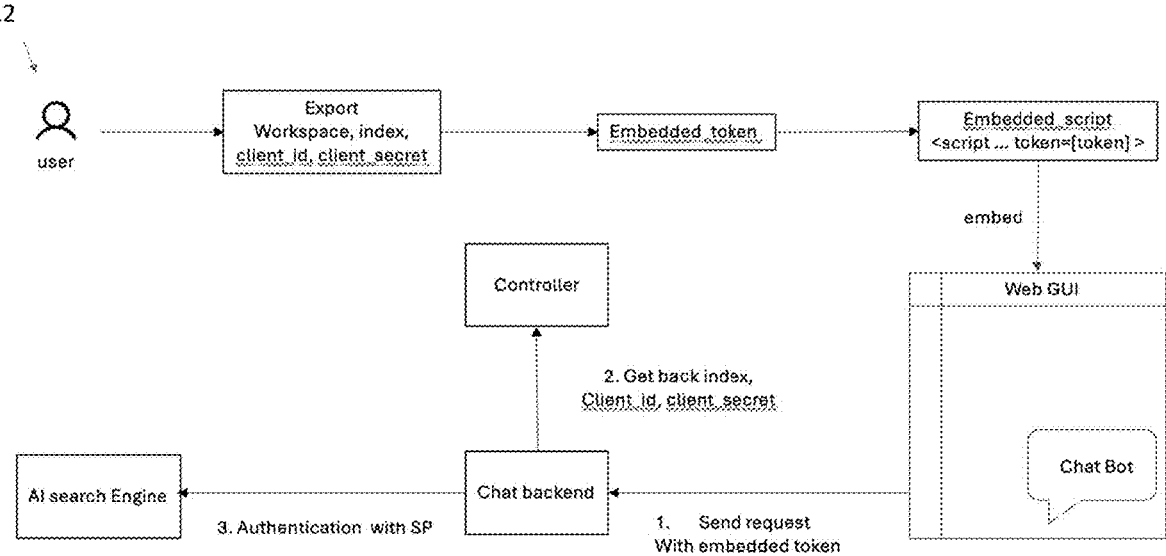
FIG. 9 is a flow chart for operating a chat bot for the AI powered search platform of FIG. 1.

Exemplary secured and embeddable interfaces of the search and chart bot may be as illustrated with particular regard to FIG. 9 by way of non-limiting example. In exemplary embodiments, role-based access control ("RBAC") may be utilized to configure and control search interfaces and chat bots. In this way, only authorized users may be able to connect the search interface and chat bot to their entitled index collections and related data.

System Security and Data Privacy

Figure 10:
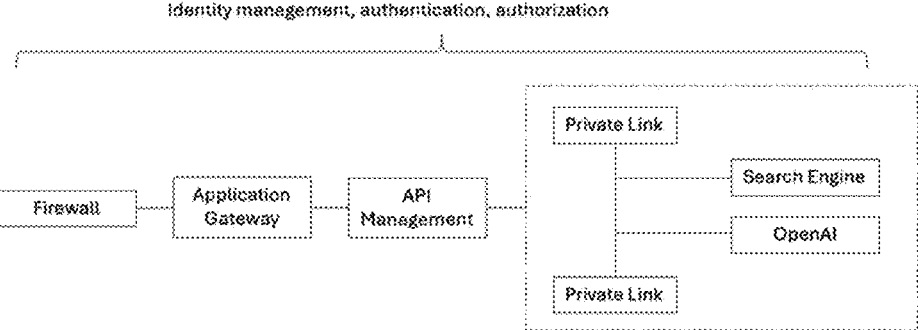
FIG. 10 is a schematic diagram for a data security and privacy module for the AI powered search platform of FIG. 1.

Data security and privacy are important aspects of AI operations. The platform 10 may integrate network security, data segregation, identity management, privileged access, and compliance with regulation features. Access control may be configured at the index and/or document levels. An exemplary identity management, authentication, authorization schema is illustrated with particular regard to FIG. 10.

Network security features may include, for example without limitation, virtual network and/or private endpoint. Identity and access features may include, for example without limitation, role-based access control (RBAC) and/or active directory (AD) access. Data security features may include, for example without limitation, encryption at rest, encryption in transit, data sovereignty, logical storage isolation, customer managed keys, privacy standards, and/or no customer data for model training. Ethical AI features may include, for example without limitation, content moderator control and/or responsible AP principles. Compliance features may include, for example without limitation, standards and/or certifications.

Figure 11:
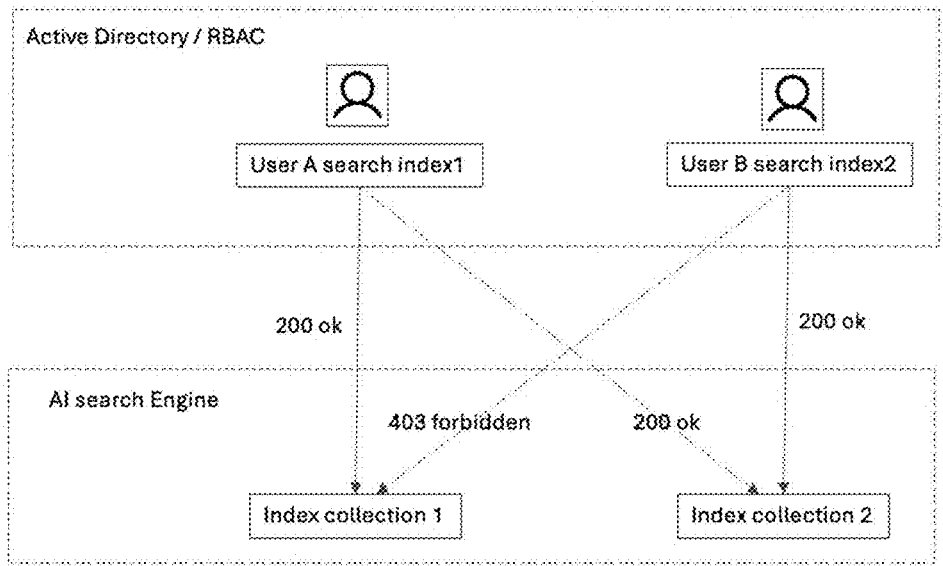
FIG. 11 is a schematic diagram for a user access and control module for the AI powered search platform of FIG. 1.

Access control may be based on each user's role, such as illustrated with particular regard to FIG. 11, by way of non-limiting example. For the access control at index level, users 12 may be allowed to access the indexes they are entitled to. User A may be allowed to access both indexes while user B may only be allowed to access index 1, by way of non-limiting example. User IDs and/or private data tokens may be issued by the system 10 which are submitted by users 12 upon access to the platform 10 for verification prior to accessing certain aspects of the system 10, such as part of a login process.

Figure 12:
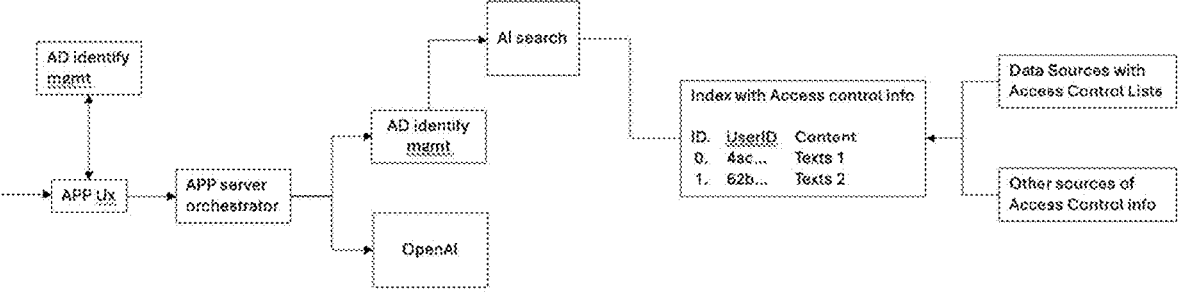
FIG. 12 is a flow chart for document level access control for the AI powered search platform of FIG. 1.

Alternatively, or additionally, access control may be implemented at the document level, such as illustrated with particular regard to FIG. 12, by way of non-limiting example. The index structure within AI search engine 14 may facilitate identity and access management. Furthermore, extra string collection fields may be incorporated to store user 12 and group identifiers in conjunction with document content. Data Lake storage may be integrated with Active Directory for access control over individual files and folders.

When security filtering is activated, users 12 may only be able to access data within the index collections they have been granted access to, such as based on RBAC. The index schema of the data may include a field of ID. A user 12 with an ID may be able to search and retrieve documents that match the user's 12 ID and/or group memberships, by way of example. User ID and/or group memberships may be established based on authenticated login information, by way of non-limiting example.

The retrieval augmented generation ("RAG") pattern may be integrated with AD in API servers, for example. Documents obtained from the search may be filtered by the system 10 based on the logged-in user's identity or group memberships. When security filtering is activated, users 12 are only able to access data within the knowledge base that they have been granted access to.

Figure 13:
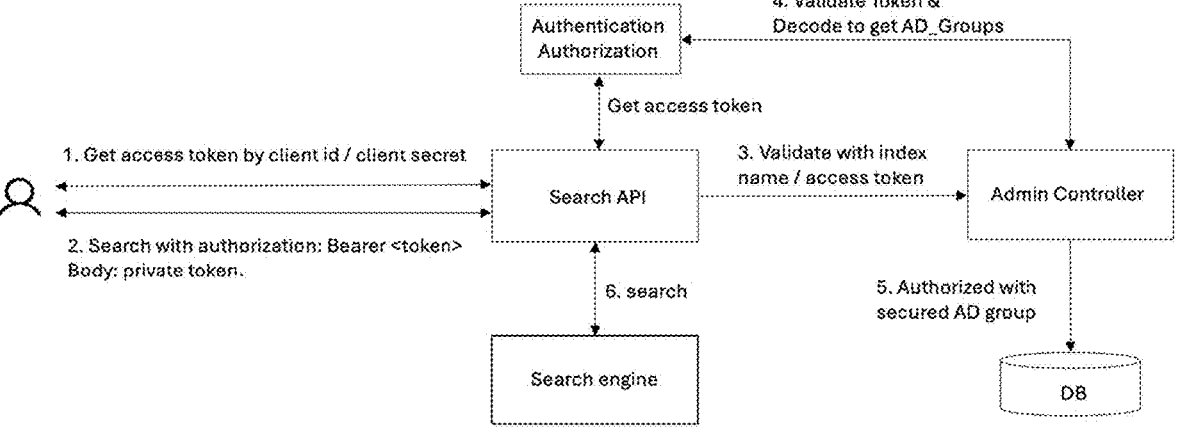
FIG. 13 is a flow chart for secured search operations for the AI powered search platform of FIG. 1.

Private data management and search are illustrated with particular regard to FIG. 13. In steps 1 and 2, the user 12 may request an access token and may submit query statements. In step 3, the search API may verify the token and index name. In step 4, the admin controller may verify the token and membership of the AD group. in step 5, the AD group may check the entitlement, and, in step 6 the search may be performed be the engine 14 and/or system 10, and the results may be returned to the user 12. The results may, before returning to the user, be processing using one or more OpenAI or other third-party tools, such as generative summaries of data, graph creation, table creation, image creation, formatting, combinations thereof, or the like.

Data Enrichment and Analytics

Figure 14:
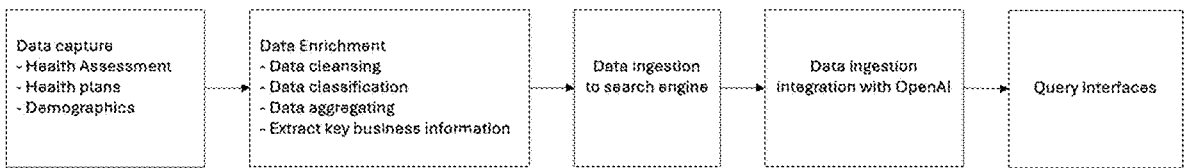
FIG. 14 is a flow chart for operational learning and improvement for the AI powered search platform of FIG. 1.

As illustrated with particular regard to FIG. 14, data capture, document classification, and extraction stages where documents are aggregated, categorized, tagged, and meaningful entities are extracted from documents may be performed by the system 10. The data intelligence and enrichment processes may refine, improve, and enhance the data sets with addition of new attributes.

The schema illustrated with particular regard to FIG. 15 may be used in capturing query history for post search analytics. The analytics may be used for marketing segmentation and targeting, as well as feedback to improve systems in terms of capacity planning and performance enhancement, by way of non-limiting example.

A notable, but non-limiting, advantage of the system 10 is that certain tools available from, and/or similar to those provided by, third parties, such as but not limited to OpenAI, may be incorporated into the system 10 without actually providing data directly to OpenAI or other such third parties. This may enhance privacy, security, compliance, combinations thereof, and the like. Such tools may include, by way of example and without limitation, intent detection and/or generative summarization.

Any embodiment of the present invention may include any of the features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention.

Certain operations described herein may be performed by one or more electronic devices. Each electronic device may comprise one or more processors, electronic storage devices, executable software instructions, combinations thereof, and the like configured to perform the operations described herein. The electronic devices may be general purpose computers or specialized computing devices. The electronic devices may comprise personal computers, smartphones, tablets, databases, servers, or the like. The electronic connections and transmissions described herein may be accomplished by one or more wired or wireless connectively components (e.g., routers, modems, ethernet cables, fiber optic cable, telephone cables, signal repeaters, and the like) and/or networks (e.g., internets, intranets, cellular networks, the world wide web, local area networks, and the like). The computerized hardware, software, components, systems, steps, methods, and/or processes described herein may serve to improve the speed of the computerized hardware, software, systems, steps, methods, and/or processes described herein. The electronic devices, including but not necessarily limited to the electronic storage devices, databases, controllers, or the like, may comprise and/or be configured to hold, solely non-transitory signals.

What is claimed is:

1. A computer-implemented method comprising:

providing an artificial intelligence powered search platform ("platform") for providing end-to-end services in digital healthcare, said platform comprising one or more servers electronically storing software instructions, which when executed, establish a plurality of data collection pipelines, a vector represented data lake comprising one or more databases, and an intent-detecting search engine, wherein said platform is in electronic communication with a plurality of user electronic devices and a plurality of data sources;

onboarding users by way of a self-service portal forming part of the platform, including establishing profiles for each of the users, establishing access attributes for the users such that each of the profiles is associated with a respective one of a plurality of candidate roles, establishing workspaces for each of the users such that each of the profiles is associated with a respective workspace, and linking each of the workspaces to a respective one of the profiles for an associated one of the users such that each of the workspaces is associated with at least one of the plurality of candidate roles;

gathering data from the plurality of data sources by way of the plurality of data collection pipelines, said plurality of data sources comprising websites and databases of documents, each of said plurality of data sources being healthcare affiliated;

processing the gathered data by way of the plurality of data collection pipelines, including transformation, enrichment, and ingestion of said gathered data into one or more common formats to arrive at processed data;

for the processed data from each of the plurality of data sources, on a source-by-source basis, assigning at least one of a plurality of candidate user attributes to the data gathered from the respective one of the plurality of data sources, said candidate user attributes comprising user roles;

storing the processed data at the vector represented data lake with the assigned user attributes;

receiving initial user search queries from the user electronic devices, and on a query-by-query basis:

processing the initial user search queries using the intent-detecting search engine to develop intent-inferred search queries;

receiving profile information, including the user attributes, associated with the profiles associated with the initial user search queries;

searching the vector represented data lake in accordance with the intent-inferred search queries and the user attributes, including the associated roles, to generate search result data such that the search results data is limited to the processed data at the vector represented data lake associated with the assigned user attributes matching the user attributes retrieved for the profile associated with the queries;

generating summaries of the search result data, including direct links to the websites of, and converted, human consumable formatted versions of the documents of the databases of, the plurality of data sources used to create the summaries; and providing the summaries to the user electronic devices from which the initial user search queries originated for display.

2. The method of claim 1 wherein:

the plurality of data collection pipelines comprise web crawlers, pull APIs, and a file upload option.

3. The method of claim 2 wherein:

the web crawlers are configured to, when executed, crawl static and dynamic web pages across domains, including embedded content, and exclude HTML tags, path patterns, and XPath; and the file upload options is configured to, when utilized, automatically recognize file format, provide optical character recognition (OCR), and extract images and tables in markdown format.

4. The method of claim 3 wherein:

the web crawlers comprise dedicated crawlers.

5. The method of claim 1 wherein:

storing a backup copy of the vector represented data lake at one or more backup databases forming part of the platforming and located in a different cloud region from the vector represented data lake.

6. The method of claim 1 wherein:

the intent-detecting search engine provides semantic analysis, intelligent autocomplete, filter application, and image recognition as part of processing the initial user search queries to develop the intent-inferred search queries.

7. The method of claim 1 further comprising:

linking a natural language search option and a chat bot to each of the workspaces, wherein the initial user search queries are received by way of the natural language search option and the chat bot.

8. The method of claim 7 further comprising:

automatically scheduling testing and verification tasks for the workspaces, including automatically generating and testing a search bar for the natural language search option and a window for the chat bot at the workspaces for testing.

9. The method of claim 1 further comprising:

assigning and storing a user ID and private data token to each of the users;

receiving a submitted user ID and private data token from each of the user electronic devices; and verifying the submitted user ID and private data token against the user ID and private data token as part of a login process.

10. The method of claim 1 further comprising:

providing query history to the intent-detecting search engine, where the intent-detecting search engine contextually analyses the uploaded query history; and updates search indexing based on said contextual analysis.

11. The method of claim 1 further comprising:

the platform comprises a self-service portal for multiple tenants.

12. The method of claim 1 wherein:

processing the data gathered from the plurality of data sources includes processing the data by embedded models and uploading to the vector represented data lake.

13. The method of claim 12 wherein:

processing the data gathered from the plurality of data sources includes:

chunking at least some of the data; and reformatting the chunked data into the one or more common formats.

14. The method of claim 13 further comprising:

the step of processing the data by the embedded models and uploading to a vector database comprises:

optically recognizing characters and words; and vector indexing the recognized words.

15. The method of claim 1 wherein:

the summaries are provided, at least in part, by one or more generative AI models forming part of said platform.

16. A system for providing an artificial intelligence ("AI") powered search platform for providing end-to-end services in digital healthcare, said system comprising:

the platform, wherein the platform is in electronic communication with a plurality of user electronic devices and a plurality of data sources and comprises one or more non-transitory electronic storage devices storing software instructions, which when executed, configure one or more processor to: perform the method of claim 1.

* * * * *